United States Patent [19]
Jones et al.

[11] Patent Number: 5,250,500
[45] Date of Patent: Oct. 5, 1993

[54] HERBICIDAL COMPOSITIONS CONTAINING TETRAPOTASSIUM PYROPHOSPHATE AS SPRAY ADJUVANT

[75] Inventors: Travis R. Jones; E. Robert Gates, both of Memphis, Tenn.

[73] Assignee: Floratine Products Group, Collierville, Tenn.

[21] Appl. No.: 929,136

[22] Filed: Aug. 13, 1992

Related U.S. Application Data

[63] Continuation-in-part of Ser. No. 153,805, Feb. 8, 1988, abandoned.

[51] Int. Cl.$^5$ .................. A01N 25/00; A01N 59/26; A01N 55/02; A01N 57/04
[52] U.S. Cl. .................. 504/165; 504/192; 504/206; 504/352; 71/DIG. 1
[58] Field of Search ............. 71/97, DIG. 1; 504/192, 504/206, 352

[56] References Cited

U.S. PATENT DOCUMENTS

| | | | |
|---|---|---|---|
| 2,678,265 | 5/1954 | Schwerdle | 71/10.5 X |
| 3,660,071 | 5/1972 | Gould et al. | 71/65 |
| 3,852,058 | 12/1974 | Hoffman | 71/118 |
| 4,008,065 | 2/1977 | Hauschild | 71/DIG. 1 |
| 4,059,325 | 11/1977 | Johnson | 71/97 |
| 4,059,435 | 11/1977 | Johnson | 71/105 |

*Primary Examiner*—Allen J. Robinson
*Assistant Examiner*—S. Mark Clardy
*Attorney, Agent, or Firm*—Richard C. Litman

[57] ABSTRACT

Herbicidal compositions comprising a post-emergence herbicide and tetrapotassium pyrophosphate as the spray adjuvant. The compositions are suitable as foliar sprays for controlling undesirable vegetation without causing damage to crops. The tetrapotassium pyrophosphate spray adjuvant has surfactant and plant nutrient characteristics and functions synergistically with the herbicide to increase its level of absorption into plant tissues and to stimulate both the target and non-target plant species to growth responses for increased herbicide efficacy.

9 Claims, No Drawings

HERBICIDAL COMPOSITIONS CONTAINING TETRAPOTASSIUM PYROPHOSPHATE AS SPRAY ADJUVANT

CROSS-REFERENCE TO RELATED APPLICATION

This application is a continuation-in-part of parent application Ser. No. 153,805, filed Feb. 8, 1988, now abandoned.

BACKGROUND OF THE INVENTION

1. Field of the Invention

The present invention relates to an agricultural spray adjuvant for use with herbicides. More particularly, the invention relates to the use of tetrapotassium pyrophosphate as the spray adjuvant in herbicidal compositions to increase the absorption and overall efficacy of post-emergence herbicides.

2. Description of the Prior Art

Herbicidal compositions in the form of dusts or liquids frequently include a surface-active agent of the kind referred to in the art as wetting, dispersing, or emulsifying agents. These agents permit the compositions to be readily dispersed in water to provide aqueous solutions for convenient spray applications. The surface-active agents employed for this purpose can be of the anionic, cationic, or nonionic type and include, for example, ethylene oxide condensation products with alkyl phenols or long-chain alcohols such as polyoxyethylated octyl phenol or stearyl alcohol, polyethylene oxides, the alkali metal or amine salts of an unsaturated fatty acid such as sodium oleate and dimethylamine oleate, the sulfonated animal and vegetable oils such as sulfonated fish and caster oils, sulfonated petroleum oils, sulfonated acyclic hydrocarbons, sodium salts of sulfonated condensation products of naphthalene and formaldehyde, the alkaline earth salts or amine salts of alkylbenzenesulfonates, sodium alkyl aryl sulfonates, partially esterified polyhydric alcohols such as diglycol monostearate, soluble sulfates such as sodium lauryl sulfate, quaternary ammonium compounds such as alkyl dimethylbenzyl ammonium chloride and the like. For further examples of other suitable surface-active dispersing agents, reference is made to U.S. Pat. No. 3,852,058 to Huffman and the publication "Detergents and Emulsifiers Annual" by John W. McCutcheon Inc., Morristown, N.J.

While herbicidal compositions containing the aforementioned agents generally promote a more even distribution of the herbicide when applied as foliar sprays, certain limitations of each type of spray additive have been recognized in the art. One such problem associated with the use of these spray adjuvants in herbicidal compositions has been the inability of the target plant tissue to absorb effective amounts of the herbicide based on a single application. The proposed remedy to this problem has been to increase the application dosage in an attempt to facilitate the desired absorption. However, this results in the inefficient use of the herbicide which can prove to be uneconomical and wasteful of materials. Also, the use of excessive quantities of certain herbicides can cause undue foliage "burn" or plasmolysis due to the retention of the herbicide on the leaf surface for prolonged periods of time. Besides this deleterious effect to target plant leaves, which may be considered as merely cosmetic, relatively high levels of certain herbicide and adjuvant residues lingering on non-target agronomic species to which they may be applied can result in increased crop damage and can even poison the soil permanently.

Another limitation associated with the use of conventional spray adjuvants in herbicidal compositions has been that of temperature restrictions during the application season. For example, as temperatures rise to 85° and above, spraying operations have to be suspended in many instances to avoid leaf burn due to poor uptake of the herbicide by plants at such elevated temperatures. Moreover, it should be noted that most spray additives are preferably used in conjunction with post-emergence herbicides and the usual time for many of these post-emergence applications is in late spring and summer. This is the time when day temperatures reach levels that cause both target and non-target plant species to be more likely stressed and, therefore, less receptive to foliar uptake of non-nutrient materials. Further, application of herbicides during periods when spray ceiling temperatures are lowered often compounds the problem of controlling weeds because other conditions such as increased field moisture and humidity, which generally accompany lower temperatures, contribute to the growth of existing weeds, as well as the germination and subsequent emergence of greater numbers of weed and grass species. In addition, post-emergence herbicides are generally ineffective when applied at temperatures below 70°–75° F. or at very high temperatures, 95° F. and higher, because the possible pathways into the plants are substantially cut off under these conditions, making absorption of the herbicide extremely difficult.

Since the effectiveness of a given herbicide largely depends on its ability to enter the stomata of target plants, the development of herbicidal spray additives in the art has necessarily focused on those selective additives which have experimentally demonstrated their capacity to increase the overall uptake of a particular herbicide. However, there is a need in the art for an improved herbicidal spray adjuvant which addresses the environmental conditions under which the herbicidal compositions are conveniently applied, as well as the physiological characteristics of target and non-target plant species themselves.

SUMMARY OF THE INVENTION

Accordingly, it is an object of the present invention to provide an improved herbicidal spray adjuvant which will function synergistically with herbicides to increase their levels of absorption into target plants and improve their overall effectiveness.

It is also an object of the invention to provide a herbicidal composition containing a spray adjuvant which has plant nutrient characteristics to stimulate both the target and non-target plant species to growth responses for increased herbicide efficacy.

It is among the additional objects of the present invention to provide a herbicidal composition suitable for application throughout the spraying season under a wider range of normally adverse conditions comprising a spray additive having surfactant properties to promote the even distribution of the herbicide and to facilitate the opening of leaf stomata for increased uptake of the herbicide into plan tissues.

These and other objects ar accomplished in accordance with the present invention which provides a herbicidal composition suitable as a foliar spray comprising an effective amount of a post-emergence herbicide and tetrapotassium pyrophosphate (TKPP) as the spray adjuvant. The spray adjuvant of the present invention has been found to be compatible with a wide range of post-emergence herbicides in current use and has been demonstrated to synergistically work in conjunction with such herbicides to make the target plant species more susceptible to the effects of the herbicide. Also, the herbicidal compositions of the present invention serve to make the non-target species less effected by both the herbicide and the spray adjuvant.

While U.S. Pat. No. 4,008,065 to Hauschild, discloses the use of TKPP as an adjuvant in granulated fertilizer compositions based upon alkali-containing calcined phosphates, no correlation can be drawn from this prior art disclosure and the surprising discovery that forms the basis of the present invention. Moreover, since the chemical relationship between TKPP and the herbicides employed in the present invention is an especially complicated one, and since substantially no common areas of activity or selectivity have been taught in the prior art to exist between herbicides and fertilizers, the unexpected effectiveness of the present herbicidal compositions could in no way be predicted from or suggested by the Hauschild patent.

In field trials utilizing tetrapotassium pyrophosphate as the herbicidal spray adjuvant, the present compositions consistently provide an improved kill ratio on target species, greater crop tolerance, and a higher temperature ceiling for field spray applications than the herbicidal formulations currently available. Moreover, suitable application of the herbicidal compositions of the present invention as a foliar spray has been shown to significantly reduce or eliminate the incidence of "cosmetic burn" in non-target agronomic species over a broader temperature range.

The above advantages, as well as further objects, features and aspects of the present invention, will be more fully appreciated by reference to the following detailed description.

DETAILED DESCRIPTION OF THE INVENTION

The class of herbicides employed in the present compositions preferably comprises those compounds which are known to show activity as post-emergence herbicides. Post-emergence herbicides are ordinarily applied after the plants have emerged and during their growth period. Examples of such herbicides suitable for use in the present invention include diphenyl ether derivatives such as 2-chloro-4-trifluoromethyl-3'-ethoxy-4'-nitrodiphenyl ether: carboxylic acids and their salts such as 5-[2-chloro-4-(trifluoromethyl)phenoxy]-2-nitrobenzoic acid and its sodium salt: carboxylic acid esters such as ethyl 2-[[[4-chloro-6-methoxy-2-pyrimidinyl)amino]carbonyl]amino]sulfonyl-benzoate and butyl 2-[4-[[5-(trifluoromethyl)-2-pyridinyl]oxy]-phenoxy]propanoate; substituted urea such 3-(2-trifluoromethylphenyl)-1,1-dimethylurea and 3-(3,4-dichlorophenyl)-1-methoxy-1-methylurea; triazines derivatives such as 2,4-diamino-6-chloro-N-ethyl-N'-(1-methylethyl)-1,3,5-triazine, 4-amino-6-(1,1-dimethylethyl)-3-(methylthio)-1,2,4-triazin-5(4H)-one and 2-[[4-chloro-6-(ethylamino)-1,3,5-triazin-2-yl]amino]-2-methyl-propanenitrile; glycine derivatives such as N-(phosphonomethyl)-glycine and its isopropylamine salt; 1,1'-dimethyl-4,4'-bipyridinium and its dichloride derivative; 3-(1-methylethyl)-1H-2,1,3-benzothiadiazin-4(3H)-one 2,2-dioxide; 2-[1-(ethoxyimino)butyl]-5-[2-(ethylthio)propyl]-3-hydroxy-2-cyclohexen-1-one; monoeodium and disodium methanearsonate and the like. Further examples of herbicides which may be employed in the present invention are set forth in U.S. Pat. No. 4,059,435.

In addition to the herbicides set forth hereinabove, other plant-regulating agents which are referred to in the art as defoliants have exhibited increased efficacy when used in conjunction with the spray adjuvant of the present invention. Suitable defoliants include s,s,s-tributylphosphorotrithioate, N-phenyl-N'-1,2,3-thiadiazol-5-yl urea, and 7-oxabicyclo [2,2,1] heptane-2,3-dicarboxylic acid and the like, for example.

The present invention is based on the discovery that the overall efficacy of herbicidal compositions suitable for spraying may be synergistically improved by incorporation of tetrapotassium pyrophosphate $K_4P_2O_7$ as the adjuvant. The effectiveness of tetrapotassium pyrophosphate (TKPP) as a herbicidal spray adjuvant is completely unexpected since an examination of other closely related plant nutrient materials yielded results which fell far short of the selective properties of the present invention. For instance, in field trials employing monopotassium phosphate $KH_2PO_4$, dipotassium phosphate $K_2HPO_4$, tripotassium phosphate $K_3PO_4$, and potassium tripolyphosphate $K_5P_3O_{10}$ as spray additives, these alkali phosphates lacked the overall ability to consistently reduce the surface tension on plant leaves. Also, herbicidal compositions containing these phosphate materials yielded rather sporadic results when spray rates was decreased to amounts lower than 12 gallons per acre, which are generally the necessary rates of application for aerial administration.

It appears that the TKPP adjuvant provides a source of nutrients for both target and non-target plant species to stimulate them to a immediate growth response for a short period of time until the herbicide used in the practice of the present invention is able to exert its selective activity by assimilation into the metabolic system of the plant species. While the target species cannot metabolize the absorbed herbicide and is destroyed, the non-target agronomic species through improved growth functions in the presence of the TKPP nutrient is better able to metabolize the selective herbicide and establish a tolerance to its effect.

The compositions of the present invention are preferably prepared by admixing TKPP in powder or granular form with an aqueous solution of the herbicide to form a liquid concentrate formulation. This liquid formulation which may contain up to about 5.5 lbs. of TKPP in 1.0 gallon of the concentrate can then diluted with the desired amount of water in a mixing tank or sprayer and thoroughly mixed prior to application as a foliar spray. Dilution ratios may vary, but generally the present spray formulations will contain about 2.0–2.5 lbs. of TKPP per gallon of the herbicidal product to achieve a preferred application rate of about 0.25 lb. TKPP per acre.

The present herbicidal sprays are applied to the area to be treated for undesirable plant growth at application rates sufficient to destroy existing undesired vegetation, such as weeds and unwanted grasses. The rates of application will, of course, vary depending on the type of equipment employed, the condition of the area treated, the particular type and stage of development of the unwanted plants, and like factors. A preferred rate of application for the post-emergence herbicides employed in the present invention is from about 0.1 to about 10 pounds per acre using spray volumes of not less than 10 gallons of water per acre.

Since the tetrapotassium pyrophosphate adjuvant serves as both a plant nutrient and surface-active agent, the incorporation of other carrier or auxiliary materials in the present herbicidal compositions is not critical to the attainment of the improved results obtained by the present invention. However, it is possible to substitute a very minor portion of the pyrophosphate with a previously known surfactant to provide further emulsion stability under certain selective conditions. For instance, it was found that the use of an adjuvant mixture consisting of about 99.5%, preferably 99.65%, of TKPP and about 0.50%, preferably 0.35%, of diglycol stearate improved the liquid consistency of certain herbicidal sprays for selective weed control.

For some applications, it may be desirable to include pre-emergence herbicides and other pest control agents, such as insecticides and fungicides in the herbicidal compositions of the present invention.

The following examples demonstrate the improved herbicidal properties of the compositions of the present invention but are not intended to be limiting in any way. All parts and percentages are designated by weight unless otherwise indicated.

tossed hoops, each having a diameter of one meter. This evaluation was repeated twice and the results recorded.

The rating index with respect to crop damage, observed as "cosmetic burn" on the 3-4" seedling cotton, was established by visual examination of 3 random crop samplings, each taken within 10 row feet. The relative rating scale for this burn index is indicated by numbers as follows:

| | |
|---|---|
| 1-2 | No speckling to very slight speckling on crop leaves. |
| 3-4 | Large specks, slight crinkling on leaf edges in 25-30% of crop. |
| 5-6 | Heavy speckling, large spots; edge crinkling in 50-60% of crop. |
| 7-8 | Heavy leaf burn in 70-80% of crop. |
| 9-10 | Heavy leaf burn on virtually all leaves - major crop damage. |

Table I gives the observed data for the test composition without TKPP at the standard rate of application of 2.0 lbs. per acre and Table II records the corresponding data when the composition containing TKPP as the adjuvant is applied at a reduced rate of 1.33 lbs. per acre. The rate of application for the TKPP adjuvant amounted to 0.25 lb. per acre.

TABLE I

| TARGET SPECIES | STAGE | % KILL 4 DAYS | % KILL 5 DAYS | % KILL 7 DAYS | CROP DAMAGE |
|---|---|---|---|---|---|
| Johnsongrass | 2> " | 22 | 28 | 48 | 8 |
| Dallasgrass | 2< " | 26 | 36 | 78 | |
| Crabgrass | 2> " | 29 | 41 | 81 | |
| Cocklebur | 2> " | 31 | 44 | 84 | |

TABLE II

| TARGET SPECIES | STAGE | % KILL 4 DAYS | % KILL 5 DAYS | % KILL 7 DAYS | CROP DAMAGE |
|---|---|---|---|---|---|
| Johnsongrass | 2> " | 58 | 84 | 91 | 2 |
| Dallasgrass | 2< " | 63 | 83 | 88 | |
| Crabgrass | 2> " | 78 | 92 | 96 | |
| Cocklebur | 2> " | 72 | 88 | 93 | |

EXAMPLE 1

Post-emergence field tests were conducted to evaluate the herbicidal activity of spray compositions comprising a mixture of monosodium methanearsonate (MSMA) and disodium methanearsonate (DSMA) as the herbicide, with and without the tetrapotassium pyrophosphate (TKPP) adjuvant of the present invention at different rates of application.

The above compositions were separately evaluated for control of the target species Johnsongrass, Dallasgrass, crabgrass, and cocklebur in the presence of cotton crop. Seeds of the designated crop and weeds are allowed to germinate under field conditions and after 2 weeks the fields are treated with the test compositions. The compositions containing the MSMA/DSMA herbicide are diluted with water and sprayed over the planted fields at the rates of 1.33 lbs. (MSMA/DSMA) per acre when employing the TKPP adjuvant, and 2.0 lbs. per acre without the TKPP adjuvant, using a spray volume of 16 gallons per acre.

The 2-week old weeds at growth stages of around 2 inches are observed 4, 5 and 7 days after application of the test compositions and the results recorded.

The phytotoxic effect of the compositions, evaluated on the basis of % kill, was established by physical counts taken within the confines of three randomly Table II clearly demonstrates that even with a reduction of the standard rate of herbicide application by 33%, the introduction of TKPP shows both an unexpected increase in the efficacy of the herbicide, as well as a dramatic decline in crop damage.

EXAMPLE 2

Following the general procedure as set forth in Example 1, with the exception that 2-chloro-4-trifluoromethyl-3'-ethoxy-4'-nitrodiphenyl ether (Oxyfluorfen) was used as the herbicide, other text compositions were evaluated for comparative purposes.

Table III sets forth field test data obtained by spraying an aqueous solution of Oxyfluorfen on cocklebur, prickly sida, and morningglory weeds and cotton crop at advanced growth stages. The growth stage is determined by counting the average number of leaves. The rate of application is 0.5 lb. per acre which is the recommended rate specified for this herbicide. The spray volume utilized is 16 gallons per acre to establish control percentages in this test.

TABLE III

| TARGET SPECIES | STAGE LEAF | % CONTROL AFTER 7 DAYS |
|---|---|---|
| Cocklebur | 4 leaf | 48 |
| Prickly Sida | 2 leaf | 54 |
| Morning Glory | 6 leaf | 52 |

The observed data for Oxyfluorfen when applied as an aqueous spray at a half rate of 0.25 lb per acre demonstrates reduced weed control as can be seen from Table IV.

TABLE IV

| TARGET SPECIES | STAGE LEAF | % CONTROL AFTER 7 DAYS |
|---|---|---|
| Cocklebur | 4 leaf | 18 |
| Prickly Sida | 2 leaf | 29 |
| Morning Glory | 6 leaf | 21 |

Adding a standard paraffinic oil surfactant to the above Oxyfluorfen solution and applying the test composition at a half rate of 0.25 lb. per acre does not result in a substantially increase herbicidal effectiveness as shown in Table V.

TABLE V

| TARGET SPECIES | STAGE LEAF | % CONTROL AFTER 7 DAYS |
|---|---|---|
| Cocklebur | 4 leaf | 36 |
| Prickly Sida | 2 leaf | 42 |
| Morning Glory | 6 leaf | 40 |

Table VI shows a dramatic increase in herbicidal efficacy with the addition of the TKPP adjuvant of the present invention to an aqueous solution of Oxyfluofen. The herbicidal composition of this example was applied at a rate of 0.25 lb. per acre using a spray volume of 16 gallons per acre. The rate of application for the TKPP additive is equivalent 0.25 lb. per acre.

TABLE VI

| TARGET SPECIES | STAGE LEAF | % CONTROL AFTER 7 DAYS |
|---|---|---|
| Cocklebur | 4 leaf | 68 |
| Prickly Sida | 2 leaf | 84 |
| Morning Glory | 6 leaf | 74 |

The results of reducing the rate of application for the TKPP additive to an equivalent 0.125 lb. per acre are set forth in Table VII. The following Table shows a decline in herbicidal activity and points to the criticality of the recommended rate of about 0.25 lb. per acre for the TKPP component of the present invention.

TABLE VII

| TARGET SPECIES | STAGE LEAF | % CONTROL AFTER 7 DAYS |
|---|---|---|
| Cocklebur | 4 leaf | 50 |
| Prickly Sida | 2 leaf | 63 |
| Morning Glory | 6 leaf | 54 |

EXAMPLE 3

The general procedure of Example 1 was repeated, except that a mixture of N-(phosphonomethyl)-glycine (Glyphosate) and its isopropylamine salt was used as the herbicide. The following tables of observed data demonstrate herbicidal activity at low temperatures and the effects of TKPP-containing compositions on herbicidal efficacy under comparative conditions.

Table VIII sets forth field test data obtained by spraying an aqueous solution of Glyphosate and its isopropylamine salt on horseweed, curly dock, and Purslane winter weeds at mature growth stages under relatively low temperatures. Due to early season burn down, there is no field crops present. Nighttime temperatures averaged a low 42° F. with a daytime high of 66° F. The rate of application is 1.0 lb. per acre which is the recommended rate specified for this herbicide The spray volume utilized is 16 gallons per acre to establish control percentages in this test. Percent kill was determined on the basis of physical counts taken 7 days after application of the herbicide spray within two randomly selected 10×10 ft. areas.

TABLE VIII

| TARGET SPECIES | STAGE LEAF | % KILL AFTER 7 DAYS |
|---|---|---|
| Horseweed | Mature | 3 |
| Curly Dock | Mature | 5 |
| Purslane | Mature | 12 |

The above experiment was repeated with the exception that the herbicide spray solution additionally consisted of 1% by volume of a active blend of a standard alkyl aryl polyethoxylate and a sodium alkylsulfonated alkylate surfactant. The modest improvement in herbicide activity is set forth in Table IX.

TABLE IX

| TARGET SPECIES | STAGE LEAF | % KILL AFTER 7 DAYS |
|---|---|---|
| Horseweed | Mature | 3 |
| Curly Dock | Mature | 5 |
| Purslane | Mature | 12 |

The following tables show an unexpected increase in herbicidal efficacy with the addition of the TKPP adjuvant of the present invention to an aqueous solution of Glyphosate and its isopropylamine salt. The results of applying this herbicidal composition at a rate of 1.0 lb. per acre using a spray volume of 16 gallons per acre is recorded in Table X. This test was repeated, except that the test composition was applied at a half rate of 0.5 lb. per acre, and the results set forth in Table XI. In both trials according to the present invention, the rate of application for the TKPP additive is equivalent 0.25 lb. per acre.

TABLE X

| TARGET SPECIES | STAGE LEAF | % KILL AFTER 7 DAYS |
|---|---|---|
| Horseweed | Mature | 86 |
| Curly Dock | Mature | 74 |
| Purslane | Mature | 83 |

TABLE XI

| TARGET SPECIES | STAGE LEAF | % KILL AFTER 7 DAYS |
|---|---|---|
| Horseweed | Mature | 81 |
| Curly Dock | Mature | 69 |
| Purslane | Mature | 74 |

The results set forth hereinabove fully illustrate that a substantial increase in herbicidal activity is achieved by post-emergence application of the TKPP-containing compositions of the present invention. Similar experiments with various other plant species and herbicides other than those specifically illustrated indicate that similar beneficial results may be attained by the practice of the invention on a wide variety of weeds and crops. Therefore, those skilled in the art will appreciate that various changes and modifications can be made from the generic teachings of the present disclosure without departing from the spirit of the invention. Accordingly, the foregoing illustrations are not to be interpreted as restrictive of the invention beyond that necessitated by the following claims.

We claim:

1. A herbicidal composition suitable for application as a foliar spray consisting essentially of an aqueous solution of an effective amount of a post-emergence herbicide and tetrapotassium pyrophosphate as the spray adjuvant.

2. The herbicidal composition according to claim 1 wherein the post-emergence herbicide is selected from the group consisting of monosodium methanearsenate, disodium methanearsenate and mixtures thereof.

3. The herbicidal composition according to claim 1 wherein the post-emergence herbicide is 2-chloro-4-trifluoromethyl-3'-ethoxy-4'-nitrodiphenyl ether.

4. The herbicidal composition according to claim 1 wherein the post-emergence herbicide is selected from the group consisting N-(phosphonomethyl)-glycine, its isopropylamine salt and mixtures thereof.

5. The herbicidal composition according to claim 2 wherein said post-emergence herbicide is applied at rate of about 2.0 lbs. per acre.

6. The herbicidal composition according to claim 3 wherein said post-emergence herbicide is applied at rate of about 0.5 lb. per acre.

7. The herbicidal composition according to claim 4 wherein said post-emergence herbicide is applied at rate of about 1.0 lb. per acre.

8. The herbicidal composition according to claim 1 wherein the tetrapotassium pyrophosphate spray adjuvant is applied at rate of about 0.5 lb. per acre.

9. The method of controlling the growth of undesirable plants which comprises applying to the plants an herbicidally effective amount of the composition of claim 1.

* * * * *